United States Patent
Woods et al.

(10) Patent No.: US 9,757,430 B2
(45) Date of Patent: Sep. 12, 2017

(54) BIOACTIVE COMPOSITIONS DERIVABLE FROM PLATELET CONCENTRATES, AND METHODS FOR PREPARING AND USING SAME

(71) Applicant: Cook General Biotechnology LLC, Indianapolis, IN (US)

(72) Inventors: Erik J. Woods, Indianapolis, IN (US); Christopher Taylor, Indianapolis, IN (US)

(73) Assignee: Cook General Biotechnology LLC, Indianapolis, IN (US)

( * ) Notice: Subject to any disclaimer, the term of this patent is extended or adjusted under 35 U.S.C. 154(b) by 130 days.

(21) Appl. No.: 14/469,963

(22) Filed: Aug. 27, 2014

(65) Prior Publication Data

US 2015/0064133 A1 Mar. 5, 2015

Related U.S. Application Data

(60) Provisional application No. 61/870,686, filed on Aug. 27, 2013.

(51) Int. Cl.

| | | |
|---|---|---|
| *A61K 38/21* | (2006.01) | |
| *A61K 35/16* | (2015.01) | |
| *A61K 38/19* | (2006.01) | |
| *A61K 38/20* | (2006.01) | |
| *A61K 38/18* | (2006.01) | |
| *A61K 35/14* | (2015.01) | |
| *A61K 35/19* | (2015.01) | |
| *C12N 5/00* | (2006.01) | |

(52) U.S. Cl.
CPC .......... *A61K 38/217* (2013.01); *A61K 35/19* (2013.01); *A61K 38/18* (2013.01); *A61K 38/1808* (2013.01); *A61K 38/1825* (2013.01); *A61K 38/1841* (2013.01); *A61K 38/1858* (2013.01); *A61K 38/1866* (2013.01); *A61K 38/191* (2013.01); *A61K 38/20* (2013.01); *A61K 38/204* (2013.01); *A61K 38/2006* (2013.01); *A61K 38/2053* (2013.01); *A61K 38/2066* (2013.01); *A61K 38/2086* (2013.01); *C12N 5/0018* (2013.01); *A61K 35/16* (2013.01); *C12N 2502/115* (2013.01)

(58) Field of Classification Search
None
See application file for complete search history.

(56) References Cited

U.S. PATENT DOCUMENTS

| | | |
|---|---|---|
| 2011/0027257 A1 | 2/2011 | Burnouf et al. |
| 2011/0171731 A1 | 7/2011 | Dietz et al. |
| 2012/0156306 A1 | 6/2012 | Weissman et al. |
| 2012/0269785 A1 | 10/2012 | Woods et al. |
| 2012/0276632 A1 | 11/2012 | Strunk et al. |

FOREIGN PATENT DOCUMENTS

| | | | |
|---|---|---|---|
| EP | 0 104 831 | 4/1984 | |
| WO | WO 2009/087560 A1 | 7/2009 | |
| WO | WO 2010/007502 A2 | 1/2010 | |
| WO | WO 2011127071 A1 * | 10/2011 | ............ A61K 35/16 |
| WO | WO 2013/003356 A1 | 1/2013 | |
| WO | WO 2014/076200 A1 | 5/2014 | |
| WO | WO 2014/126970 A1 | 8/2014 | |

OTHER PUBLICATIONS

Marx, Robert E; "Platelet-Rich Plasma (PRP): What Is PRP and What Is Not PRP? " Implant Dentistry, 10, 225-228, 2001.*
Boswell. Stacie, G; et al; "Platelet-Rich Plasma: A Milieu of Bioactive Factor" The Journal of Arthroscopic and Related Surgery, 28, 429-439, 2012.*
Andia, Isabel; et al; "Platelet-rich plasma for managing pain and inflammation in osteoarthritis" Rheumatology, 9, 721-730, 2013.*
Koffler, Bruce H; "Autologous Serum Therapy of the Ocular Surface with Novel Delivery by Platelet Concentrate Gel" Clinical Science, 4, 188-195, 2006.*
Amable, P. et al., "Platelet-rich Plasma Preparation for Regenerative Medicine: Optimization and Quantification of Cytokines and Growth Factors," Stem Cell Research & Therapy, Biomed Central Ltd., vol. 4, No. 3, Jun. 7, 2013, p. 67.
Anitua, E. et al., "Autologous Preparations Rich in Growth Factors Promote Proliferation and Induce VEGF and HGF Production by Human Tendon Cells in Culture," Journal of Orthopaedic Research, Orthopaedic Research Society, vol. 23, No. 2, Mar. 1, 2005, pp. 281-286.
Burnouf, T. et al., "Human Blood-Derived Fibrin Releasates: Composition and Use for the Culture of Cell Lines and Human Primary Cells," Biologicals, vol. 40, No. 1, Jan. 1, 2012, pp. 21-30.
Chou, M. et al., "Ex vivo Expansion of Bovine Corneal Endothelial Cells in Xeno-Free Medicum Supplemented with Platelet Releasate," Plos One, vol. 9, No. 6, Jun. 19, 2014, p. e99145.
Copland, I et al., The Effect of Platelet lysate Fibrinogen on the Functionality of MSCs in Immunotherapy, Biomaterials, vol. 34, No. 32, Jun. 24, 2013, pp. 7840-7850.
International Search Report and Written Opinion issued in PCT/US2014/052885, mailed Dec. 23, 2014, 11 pgs.
Ex Vivo Expansion of Conjunctival and Limbal Epithelial Cells Using Cord Blood Serum-Supplemented Culture Medium, Ang et al, Investigative Ophthalmolog & Visual Science, Aug. 2011, vol. 52, No. 9, 6138-6147.
Platelet-Rich Plasma: Quantification of Growth Factor Levels and the Effect on Growth and.Differentiation of Rat Bone Marrow Cells, Van Den Dolder et all, Tissue Engineering, vol. 12, No. 11, 2006, 3067-3073.

* cited by examiner

*Primary Examiner* — David Berke-Schlessel
(74) *Attorney, Agent, or Firm* — Woodard, Emhardt, Moriarty, McNett & Henry LLP (57) ABSTRACT

The present disclosure provides a composition comprising a bioactive fraction derived from a platelet concentrate, methods of making the bioactive fraction, and culture medium supplemented with the bioactive fraction. Preferred bioactive fractions have relatively low fibrinogen concentrations while retaining native growth factors in beneficial amounts and ratios.

24 Claims, 3 Drawing Sheets

BIOACTIVE COMPOSITIONS DERIVABLE FROM PLATELET CONCENTRATES, AND METHODS FOR PREPARING AND USING SAME

REFERENCE TO RELATED APPLICATION

The present application claim the benefit of U.S. Provisional Patent Application No. 61/870,686 filed Aug. 27, 2013 which is incorporated herein by reference in its entirety.

BACKGROUND

The present invention relates generally to the field of bioactive materials derived from animal blood platelet products, and methods of preparation and use thereof.

The administration of cells or compositions containing cells for therapeutic treatment is becoming an increasingly popular treatment modality. Such treatments may include, for example, the administration of mesenchymal stem cells (MSCs) which have the potential to differentiate into mesenchymal lineage cells including, for instance, bone, fat, cartilage, and muscle.

In order to obtain therapeutic amounts of cells for transplant it is often necessary to expand a population of cells from an initial population. The culture media used to expand the cell population supplies essential nutrients for cell metabolism, growth, and proliferation. Fetal Bovine Serum (FBS) is often used as a supplement to encourage population expansion. FBS has been a preferred supplement due to its low level of antibodies, because it contains many growth factors which stimulate cell growth and proliferation, and because it is relatively inexpensive to manufacture. However, FBS has recognized disadvantages including the risk of transmission of pathogens such as bovine spongiform encephalopathy.

Human platelet lysate (hPL) has emerged as a potential non-xenogenic alternative to FBS. hPL is derived from platelets known to contain a variety of growth factors. In addition to growth factors, current hPL isolation techniques commonly result in compositions which retain a high concentration of fibrinogen, a glycoprotein involved in clot formation. Because of their fibrinogen content and tendency to clot, current commercial hPL compositions are often used in conjunction with one or more anticoagulant additives, typically heparin. Anticoagulant additives in hPL increase the cost of hPL production and/or use and may be problematic in situations where the bioactivity of heparin is detrimental. Also, while a variety of processes for producing hPL have been proposed, attempts to achieve target compositional profiles or bioactivities for the hPL product have often led to process complexity and/or intensive equipment requirements. Significant adoption of hPL as a substitute for FBS will require economically practicable processes which nonetheless yield desirable and effective compositions.

In view of this background, needs exist for human platelet lysate compositions which are substantially free from fibrinogen, that retain growth factors beneficial to cell proliferation, and that can be readily and economically manufactured.

SUMMARY

In certain aspects of this disclosure, it has been discovered that advantageous bioactive fractions of blood-derived platelet concentrates, preferably human, can be uniquely processed from the concentrates. The bioactive fractions can have novel compositional profiles of growth factors and/or other substances present in the starting concentrates, and the processing methods can involve novel techniques for clotting and separating fractions of the concentrates and/or novel depth filtration operations to clarify liquid fractions derived from the concentrates.

In one aspect, a method for processing a platelet lysate composition includes the steps of lysing platelets of a human blood-derived concentrate containing platelets and plasma to form a lysed platelet preparation, forming a clot gel by converting fibrinogen to fibrin in the lysed platelet preparation, and compressing the clot gel so as to express liquid from the clot gel.

In another aspect, a method includes passing a liquid bioactive fraction of a blood-derived platelet concentrate comprising native components of the platelet concentrate including fibrinogen, albumin, globulin, and at least one of, and optionally all of, TGF-$\beta$1, EGF, FGF-beta, PDGF-AA, PDGF-BB, SDF-1$\alpha$, and VEGF, wherein the fibrinogen is present at a level less than 20,000 ng/mL, through at least a first depth filter, so as to remove suspended solids from the bioactive fraction. The platelet concentrate is preferably a human platelet concentrate. In preferred modes, the liquid bioactive fraction is passed through the first depth filter and also through a second depth filter, where the second depth filter optionally has a nominal micron rating that is smaller than that of the first depth filter.

In another aspect, provided is a composition comprising a bioactive fraction of a human blood-derived platelet concentrate, the platelet concentrate containing human platelets and human plasma, the bioactive fraction comprising native components of the platelet concentrate including fibrinogen, albumin, globulin, TGF-$\beta$1, EGF, FGF-beta, PDGF-AA, PDGF-BB, SDF-1$\alpha$, and VEGF. The bioactive fraction can have the fibrinogen present at a level of less than about 20,000 ng/mL, for example in the range of about 500 ng/mL to about 20,000 ng/mL, and/or the bioactive fraction, or a cell culture medium containing it, can be free or essentially free from added heparin (i.e. heparin non-native to the platelet concentrate starting material). The bioactive fraction can have levels of or ratios of growth factors as disclosed herein. In certain embodiments, the bioactive fraction is a liquid bioactive fraction and the native components include:

fibrinogen at a level of less than 20,000 ng/mL of the liquid bioactive fraction, for example in the range of about 500 ng/mL to about 20,000 ng/mL;

albumin at a level of at least 2 mg/dL of the liquid bioactive fraction;

globulin at a level of at least 1 g/dL of the liquid bioactive fraction;

TGF-$\beta$1 at a level of at least 5000 picograms/mL ("pg/mL") of the liquid bioactive fraction;

EGF at a level of at least 20 pg/mL of the liquid bioactive fraction;

FGF-beta at a level of at least 5 pg/mL of the liquid bioactive fraction;

PDGF-AA at a level of at least 200 pg/mL of the liquid bioactive fraction;

PDGF-BB at a level of at least 50 pg/mL of the liquid bioactive fraction;

SDF-1$\alpha$ at a level of at least 100 pg/mL of the liquid bioactive fraction; and VEGF at a level of at least 10 pg/mL of the liquid bioactive fraction.

The present disclosure also provides a method for preparing a bioactive composition, comprising the steps of:

adding a clotting agent to a platelet lysate composition to form a clotted material, separating clotted solids from liquid in the clotted material, and subjecting the liquid to depth sterile filtration. In some forms the method also includes packaging the bioactive composition in a sterile container.

In certain embodiments, the bioactive fraction is a liquid bioactive fraction and the native components include:

FGF-2 at a level between about 200 pg/mL to about 350 pg/mL;

EGF at a level of between about 1800 pg/mL to about 3100 pg/mL;

PDGF-AA at a level of between about 24,000 pg/mL to about 28,000 pg/mL;

PDGF-BB at a level of between about 50 ng/mL to about 80 ng/mL;

VEGF at a level of between about 500 pg/mL to about 800 pg/mL;

TGF-b at a level of between about 60 ng/mL to about 90 ng/mL; and fibrinogen at a level of less than 2.5 μg/mL.

Additional embodiments disclosed herein relate to uses of bioactive fractions or compositions described herein for cell culture, cryopreservation, or therapeutic purposes.

Still further embodiments, as well as features and advantages, will be apparent to those of ordinary skill in the art from the descriptions herein.

DETAILED DESCRIPTION

For the purpose of promoting an understanding of the principles of the invention, reference will now be made to certain embodiments and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates.

In general the present disclosure provides bioactive compositions, and methods of making bioactive compositions, which can be used for example, as cell culture supplements and/or therapeutics. The compositions of the present disclosure include compositions derived from human sources, thus overcoming problems associated with xenogenic compositions such as FBS. Furthermore, preferred compositions of the present disclosure, while retaining important growth factors and other chemical substances, have low fibrinogen content and do not require the addition of anticoagulants such as heparin to prevent problematic clotting during use.

Figure 1:
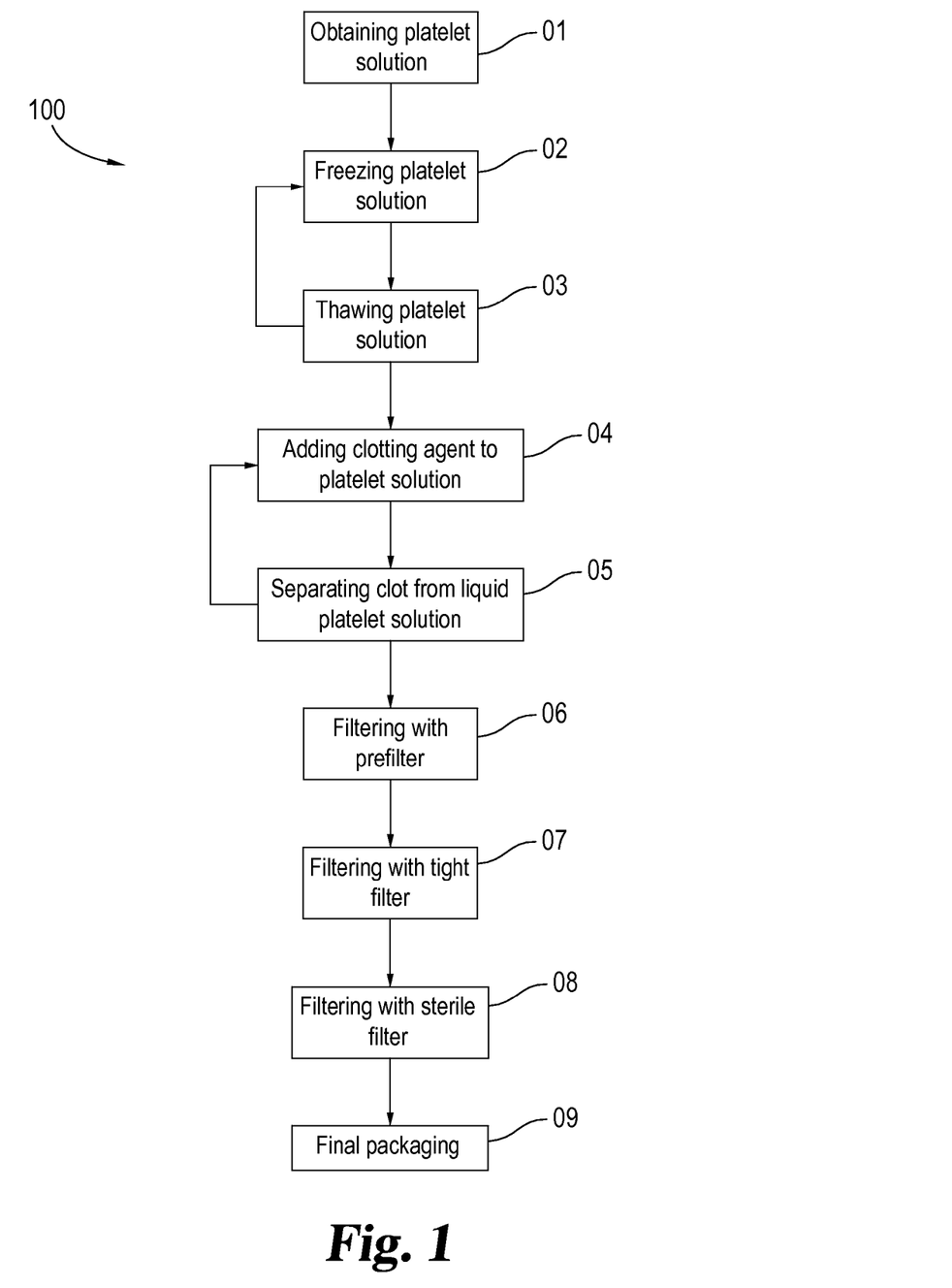
FIG. 1 illustrates a method for preparing a liquid bioactive fraction of a human platelet concentrate composition.

Turning now to FIG. 1, shown is one illustrative method 100 for preparing a bioactive fraction from a platelet concentrate composition. The method includes the steps of: obtaining a platelet concentrate 01, freezing the platelet concentrate 02, thawing the platelet concentrate 03, adding clotting agent to the platelet concentrate 04, separating clot solids from a liquid 05, filtering the liquid with a first depth filter 06, filtering the liquid with a second depth filter 07, filtering the liquid with a sterile filter 08, and packaging the liquid 09. The discussions below in some respects expand upon options for each of these depicted general steps; however, it will be understood that not all of the depicted general steps are required for all embodiments herein, and that novel methods that include features corresponding to one, some, or all of the depicted steps are contemplated as embodiments herein.

Platelet concentrate compositions used as source material for the disclosed methods and bioactive fractions may be obtained in any suitable way. As used herein, the term platelet concentrate refers to a liquid composition containing platelets that have been concentrated from a blood source. The blood source is preferably human blood, such as whole human peripheral blood. The platelet concentrate preferably includes both platelets and plasma proteins, and may be provided by platelet units obtained from whole peripheral blood of human donors by apheresis. It is envisioned that whole blood from other species, for example mammalian species, may also be used as a source for platelet concentrates to be processed as described herein. In certain embodiments, platelet units from different human or other donors can be pooled at some point during processing to obtain the bioactive fraction. In typical practice today, each human donor apheresed platelet unit has a volume of about 100 to about 500 mL, more typically about 100 to 400 mL, and contains about 100 to $500 \times 10^9$ platelets along with plasma isolated with the platelets during the apheresis procedure. Donated human apheresis platelet units have a relatively brief shelf life for use at health care facilities, typically about five days. Platelet units used in methods herein can be recently expired human apheresis platelet units obtained from health care facilities, and can optionally be stored frozen at any suitable temperature, for example about −20° C., prior to use to prepare a bioactive fraction as described herein.

In preparing the bioactive fraction, the contents of the platelets can be released by a suitable method. In some modes, the platelets are lysed by subjecting them to at least one freeze-thaw cycle to release the platelet contents, and optionally multiple freeze-thaw cycles (e.g. 2 or 3 freeze-thaw cycles). In use of a freeze-thaw cycle, the platelet concentrate can be frozen at any suitable temperature. In some aspects, the platelet concentrate is frozen at a temperature between about −10° C. and about −80° C. In specific preferred embodiments, the platelet concentrate is frozen at about −20° C. To lyse the platelets, the frozen platelet concentrate is thawed, for example in a 37° C. water bath or by other effective means, to form a "raw" platelet lysate composition. The raw platelet lysate contains the lysed platelet membranes and growth factors and other substances released from the lysed platelets. When the platelet concentrate being thawed contains plasma along with the platelets, the platelet lysate will also contain plasma, including plasma proteins therein. Other techniques for releasing platelet contents, for example activation with thrombin, may be used in certain aspects herein. However, freeze-thaw or other mechanical techniques for lysing the platelets are considered advantageous in that they do not require the addition of a non-native protein (e.g. thrombin) to the platelet concentrate, which addition both increases cost and leads to the presence of at least some of the thrombin in the downstream processed material.

The raw platelet lysate contains multiple growth factors from the platelet concentrate starting material. These can include, for example, transforming growth factor beta 1, epidermal growth factor, basic fibroblast growth factor, platelet derived growth factor AA, platelet derived growth factor BB, stromal cell-derived factor-1α, and vascular endothelial growth factor.

Transforming growth factor beta 1 (TGF-β1) is a multifunctional peptide that controls proliferation, differentiation, and other functions in many cell types. Epidermal growth factor (EGF) stimulates cellular proliferation, differentiation, and survival. Basic fibroblast growth factor (FGF-b) promotes angiogenesis, and binds to heparin which stimulates a wide variety of cells. Platelet derived growth factor AA (PDGF-AA) is a dimeric glycoprotein which regulates cell growth and division, and promotes angiogenesis. Platelet derived growth factor BB (PDGF-BB) is a dimeric glycoprotein which regulates cell growth and division, and promotes angiogenesis. Stromal cell-derived factor-1α (SDF-1α) activates leukocytes and promotes angiogenesis. Vascular endothelial growth factor (VEGF) contributes to vasculogenesis and angiogenesis.

In certain embodiments, the raw platelet lysate includes the following growth factors and amounts thereof (based on the volume of original, undiluted platelet concentrate):

about 50,000 to about 150,000 pg/ml TGF-β1, preferably about 70,000 to about 120,000 pg/ml TGF-β1; and/or about 100 to 600 pg/ml EGF, preferably about 200 to about 600 pg/ml EGF; and/or about 5 to about 250 pg/ml FGF-b, preferably about 50 to 200 pg/ml FGF-b; and/or about 500 to about 20,000 pg/ml PDGF-AA, preferably about 5000 to about 15000 pg/ml PDGF-AA; and/or about 1000 to about 20,000 pg/ml PDGF-BB, preferably about 2000 to about 15000 pg/ml PDGF-BB; and/or about 400 to 1100 pg/ml SDF-1α, preferably about 500 to about 1000 pg/ml SDF-1α; and/or about 10 to about 800 pg/ml VEGF, preferably about 100 to about 600 pg/ml VEGF.

In preferred forms, the raw platelet lysate also includes one or more components derived from plasma in the platelet concentrate starting material, including for example fibrinogen, globulins, albumen, triglycerides, glucose, sodium, calcium, and/or cholesterol. In preferred forms, the raw platelet lysate includes the following components and amounts:

about 0.5 to 2.5 g/dL globulins, preferably about 1.5 to 2.5 g/dL globulins;

about 2 to 5 g/dL albumin, preferably about 3 to 4 g/dL albumin;

about 100 to 200 mmol/L sodium, preferably about 120 to about 160 mmol/L sodium;

about 40 to 200 mg/dL triglycerides, preferably about 50 to 120 mg/dL triglycerides;

about 150 to 300 mg/dL glucose, preferably about 150 to 250 mg/dL glucose;

about 5 to 12 mg/dL calcium, preferably about 6 to 10 mg/dL calcium; and/or about 1 to 3.5 million ng/mL fibrinogen, preferably about 1.5 to 2.5 million ng/mL fibrinogen.

The raw platelet lysate can also contain other bioactive substances, for example one or more interleukins, interferons, and/or tumor necrosis factors. These interleukin(s), interferon(s) and/or tumor necrosis factor(s) may include, for example, one, some, or all of interleukin (IL)-1b, IL-6, IL-8, IL-10, IL-13, IL-17, interferon-gamma (IFN-gamma), and tumor necrosis factor-alpha (TNF-alpha).

In certain embodiments herein, the raw platelet lysate is processed to remove particulate matter, for example centrifuged, and sterilized for use as a platelet lysate product. Such sterilization can, for example, include passing the raw platelet lysate depleted of the particulate matter through a sterile filter.

In some embodiments herein, the raw platelet lysate is treated to recover a fraction thereof with a reduced fibrinogen concentration. Fibrinogen may be removed by any suitable technique, including for example by conversion to fibrin resulting in the formation of solid clot material, which can be separated from a liquid bioactive fraction. Such conversion to fibrin can be induced by the addition of a clotting agent. In accordance with some forms of practicing the disclosed methods, a clotting agent, for example a calcium chloride salt, can be added to the raw platelet lysate. Illustratively, a calcium chloride salt can be added to the raw platelet lysate in an amount between about 0.1 g and 2 g per liter of raw platelet lysate. In preferred embodiments, about 0.4 g to about 0.75 g of a calcium chloride salt is added per liter of raw platelet lysate. The combined platelet lysate and calcium chloride or other clotting agent may be placed on a shaker or otherwise agitated to ensure thorough mixing of the clotting agent with the concentrate. The resulting mixture is then allowed to form a solid clot material, in certain embodiments for a period of at least about 8 hours, or at least about 12 hours, and typically in the range of about 8 hours to about 36 hours. In preferred forms, at least a predominant amount (over 50%) of the resulting clotted material, and potentially at least 80% or at least 90% of the resulting clotted material, is constituted by a substantially homogenous clot gel. Such a substantially homogenous clot gel can exhibit a consistent gel phase throughout the material, with liquid entrained within a continuous fibrin matrix. These preferred forms of clotted material are distinct from clotted platelet concentrate materials in which a multitude of discrete solid clot particles are suspended in a liquid phase, as would be desirable for a subsequent centrifuge-based separation technique.

After a clot has formed, liquid material can be separated from solid clot material. Any suitable technique may be used for this purpose. In preferred forms, the clotted material is pressed between two or more surfaces to separate clotted solids from liquid. In cases where the clotted material exhibits the form of a substantially homogenous clot gel as discussed herein, such pressing can express the liquid from the gel material while compressing and condensing the fibrin matrix of the gel. Pressing the clotted material can in some forms be conducted in a flexible container such as a plastic bag. The clot gel can be pressed, for example manually by hand or by forced application of an implement, to one region (e.g. end) of the bag or other flexible container and the liquid expressed from the solid fibrin matrix can gather in another region (e.g. end) of the bag or other flexible container. A second bag or other container can be connected to the first bag in which the pressing occurs, either during or after the pressing, and the liquid material can be transferred to the second bag or other container. In other modes, the clot gel can be in a rigid container such as a bucket, and can by pressed by hand or with the forced application of an implement to express the liquid from the solid fibrin matrix and compress and condense the fibrin matrix.

After clotting and separation of the liquid and solid materials of the clotted platelet concentrate, the separated liquid has a reduced concentration of fibrinogen as compared to the raw platelet lysate prior to clotting. In preferred forms, the raw platelet lysate has a fibrinogen content of at least one million ng/mL, typically in the range of about 1,500,000 to 3,500,000 (1.5 to 3.5 million) ng/mL, and after clotting and separation the liquid has a fibrinogen content of less than about 50,000 ng/mL, preferably less than about 20,000 ng/mL, and more preferably less than about 10,000 ng/mL. Illustratively, this separated liquid can have a fibrinogen content in the range of about 500 ng/mL to about 20,000 ng/mL, or about 500 ng/mL to about 10,000 ng/mL. Additionally or alternatively, this separated liquid can contain less than about 5% of the fibrinogen present in the platelet concentrate prior to clotting, preferably less than about 2%, and more preferably less than about 1%. As well, this separated liquid can constitute at least about 70% of the volume of the raw platelet lysate, preferably at least about 75%, and typically in the range of about 75% to about 90%.

The fibrinogen-depleted liquid bioactive fraction recovered after the clotting of the raw platelet lysate and the liquid solid/separation separation contains multiple growth factors from the raw platelet lysate. These can include TGF-β1, EGF, FGF-beta, PDGF-AA, PDGF-BB, SDF-1α, and VEGF. In certain embodiments, this fibrinogen-depleted liquid bioactive fraction includes the following growth factors and amounts thereof from the raw platelet lysate:

about 50,000 to about 150,000 pg/ml TGF-β1, preferably about 70,000 to about 120,000 pg/ml TGF-β1;

about 20 to 800 pg/ml EGF, preferably about 400 to about 800 pg/ml EGF; and/or about 5 to about 250 pg/ml FGF-b, preferably about 50 to 250 pg/ml FGF-b; and/or about 500 to about 25,000 pg/ml PDGF-AA, preferably about 5000 to about 18000 pg/ml PDGF-AA; and/or about 1000 to about 25,000 pg/ml PDGF-BB, preferably about 2000 to about 18000 pg/ml PDGF-BB; and/or about 400 to 1000 pg/ml SDF-1α, preferably about 500 to about 900 pg/ml SDF-1α; and/or about 10 to about 600 pg/ml VEGF, preferably about 150 to about 450 pg/ml VEGF.

In other embodiments, the fibrinogen-depleted liquid bioactive fraction includes the following growth factors and amounts thereof from the raw platelet lysate:

FGF-2 (i.e. FGF-b) at a level of between about 200 pg/mL to about 350 pg/mL; and/or EGF at a level of between about 1800 pg/mL to about 3100 pg/mL; and/or PDGF-AA at a level of between about 24,000 pg/mL to about 28,000 pg/mL; and/or PDGF-BB at a level of between about 50 ng/mL to about 80 ng/mL; and/or VEGF at a level of between about 500 pg/mL to about 800 pg/mL; and/or TGF-b at a level of between about 60 ng/mL to about 90 ng/mL.

In some forms, the fibrinogen-depleted liquid bioactive fraction also has a fibrinogen content of less than 3 µg/mL, preferably less than 2.5 µg/mL.

In preferred forms, this fibrinogen-depleted liquid bioactive fraction also includes one or more components derived from plasma in the platelet concentrate starting material, including for example globulins, albumen, triglycerides, glucose, sodium, and/or calcium. Where a calcium chloride salt is used to clot the raw platelet lysate, the calcium present in the separated liquid bioactive agent can be from both the lysate and the added calcium salt. In certain embodiments, this separated liquid bioactive fraction includes the following components and amounts from the raw platelet lysate:

about 0.5 to 2.5 g/dL globulins, preferably about 1 to 2 g/dL globulins;

about 2 to 5 g/dL albumin, preferably about 3 to 4 g/dL albumin;

about 100 to 200 mmol/L sodium, preferably about 120 to about 160 mmol/L sodium;

about 40 to 70 mg/dL triglycerides, preferably about 50 to 65 mg/dL triglycerides; and/or about 150 to 300 mg/dL glucose, preferably about 150 to 250 mg/dL glucose.

As well, where a calcium chloride salt is used as a clotting agent for the raw platelet lysate, this separated liquid bioactive fraction can in some forms include calcium at a level of about 15 to 35 mg/dL, and preferably about 15 to 25 mg/dL.

In accordance with some modes of practicing the invention, the liquid bioactive fraction is passed through a sterile filter. In preferred embodiments the sterile filter comprises a 0.2 µm sterile filter. After passage through the sterile filter the liquid bioactive fraction may be sealed within a sterile container.

Certain inventive embodiments herein include filtering the recovered liquid bioactive fraction after the clotting and liquid/solid separation steps, for example to remove suspended solids such as any remaining platelet debris, cellular debris, and clot solids. In preferred modes, such filtering includes processing the liquid bioactive fraction through at least one depth filter, and preferably multiple depth filters, such as two or three depth filters of potentially differing micron ratings. In this regard, as is known and as used herein, a "depth filter" or "depth filtration" refers to a filter to filtration, respectively, that utilizes a porous filtration medium to retain particles throughout the medium, rather than just on the surface of the medium. Further, as is known and as used herein, "nominal micron rating" as applied to a filter means the particle size above which 98% of all suspended solids will be removed throughout the rated capacity of the filter. Certain inventive variants include filtration through at least one depth filter followed by at least one sterile filter. Additional inventive variants include filtration through at least two depth filters followed by at least one sterile filter. In preferred forms, the depth filter or depth filters used have a filter medium with a positive surface charge.

In certain embodiments, first and second depth filters are used in depth filtration of the liquid bioactive fraction. The first depth filter has a nominal micron rating that is larger than that of the second depth filter. In some forms, the first depth filter has a nominal micron rating between about 10 and 0.1 microns. In preferred embodiments, the first depth filter is has a nominal micron rating between 5 and 0.1 microns, even more preferably between about 3 and 0.2 microns. In certain embodiments, the first depth filter has a cellulose membrane and a filter medium comprised of cellulose fibers and an inorganic filter aid, such as diatomaceous earth, with a positive surface charge.

In certain embodiments, the second depth filter has a nominal micron rating less than that of the first depth filter, for example in some forms less than about 0.5 microns. In preferred embodiments, the second depth filter has a nominal micron rating between 0.5 and 0.001 microns, and more preferably between about 0.1 and 0.001 microns. In certain embodiments, the first depth filter has a cellulose membrane and a filter medium comprised of cellulose fibers and an inorganic filter aid, such as diatomaceous earth, with a positive surface charge.

In preferred forms, the liquid bioactive fraction, after the depth filtration or other filtration to remove suspended solids, still contains multiple growth factors from the raw platelet lysate. These can include TGF-β1, EGF, FGF-beta, PDGF-AA, PDGF-BB, SDF-1α, and VEGF. In certain embodiments, this filtered liquid bioactive fraction includes the following growth factors and amounts thereof derived from the raw platelet lysate:

about 5000 to about 75,000 pg/ml TGF-β1, preferably about 5000 to about 60,000 pg/ml TGF-β1;

about 20 to 300 pg/ml EGF, preferably about 50 to about 250 pg/ml EGF;

about 5 to about 150 pg/ml FGF-beta, preferably about 30 to 130 pg/ml FGF-b;

about 200 to about 4000 pg/ml PDGF-AA, preferably about 1000 to about 3000 pg/ml PDGF-AA;

about 50 to about 1000 pg/ml PDGF-BB, preferably about 100 to about 500 pg/ml PDGF-BB;

about 100 to 700 pg/ml SDF-1α, preferably about 300 to about 600 pg/ml SDF-1α; and/or about 10 to 400 pg/ml VEGF, preferably about 40 to about 200 pg/ml VEGF.

In preferred forms, this depth filtered or other filtered liquid bioactive fraction also still includes one or more components derived from plasma in the platelet concentrate starting material, including for example globulins, albumen, triglycerides, glucose, sodium, and/or calcium. Again, where a calcium chloride salt is used to clot the raw platelet lysate, the calcium present in the filtered liquid bioactive agent can be from both the lysate and the added calcium salt. In certain embodiments, this filtered bioactive liquid fraction includes the following components and amounts derived from the raw platelet lysate:

about 0.5 to 2.5 g/dL globulins, preferably about 1 to 2 g/dL globulins;

about 2 to 5 g/dL albumin, preferably about 3 to 4 g/dL albumin;

about 100 to 200 mmol/L sodium, preferably about 120 to about 160 mmol/L sodium;

about 50 to 120 mg/dL triglycerides, preferably about 60 to 110 mg/dL triglycerides; and/or about 150 to 300 mg/dL glucose, preferably about 150 to 250 mg/dL glucose.

As well, where a calcium chloride salt is used as a clotting agent for the raw platelet lysate, this separated bioactive liquid fraction can in some forms include calcium at a level of about 15 to 60 mg/dL, and preferably about 20 to 50 mg/dL.

The bioactive liquid fraction can also include other bioactive substances, for example one or more interleukins, interferons, and/or tumor necrosis factors. These interleukin(s), interferon(s) and/or tumor necrosis factor(s) may include, for example, one, some, or all of interleukin (IL)-1b, IL-6, IL-8, IL-10, IL-13, IL-17, interferon-gamma (IFN-gamma), and tumor necrosis factor-alpha (TNF-alpha).

As noted above, in some embodiments of methods herein, the liquid bioactive fraction is passed through at least one sterile filter, preferably after passage through the depth filter(s) or other filter(s) to remove suspended solids as discussed above. A variety of sterile filters and associated methods are known and can be used. Exemplary contaminants to be removed by the sterile filter(s) include, for example: *staphyloccus aureus, pseudomonas aeruginosa, clostridium sporogenes, candida albicans, aspergillus niger, mycoplasma*, and/or *bacillus subtilis*. The sterile filter(s) may be selected to exhibit relatively low protein binding. After sterile filtration, in preferred forms, the sterile filtered liquid bioactive fraction can have the same components as specified above for the depth filtered or other filtered liquid bioactive fraction, and also has levels of those components within the ranges specified above for the depth or other filtered liquid bioactive fraction. It will be understood, however, that some reduction in the levels of some or all of the components may occur during the sterile filtration.

In certain preferred embodiments, a sterile liquid bioactive fraction composition, which can be obtained by the above-described steps of platelet lysis, fibrinogen depletion, and depth or other filtration to remove suspended particulate, includes:

fibrinogen at a level of less than 20,000 ng/mL of the liquid bioactive fraction, for example in the range of about 500 ng/mL to about 20,000 ng/mL;

albumin at a level of at least 2 mg/dL of the liquid bioactive fraction;

globulin at a level of at least 1 g/dL of the liquid bioactive fraction;

TGF-β1 at a level of at least 5000 pg/mL of the liquid bioactive fraction;

EGF at a level of at least 20 pg/mL of the liquid bioactive fraction;

FGF-beta at a level of at least 5 pg/mL of the liquid bioactive fraction;

PDGF-AA at a level of at least 200 pg/mL of the liquid bioactive fraction;

PDGF-BB at a level of at least 50 pg/mL of the liquid bioactive fraction;

SDF-1α at a level of at least 100 pg/mL of the liquid bioactive fraction; and

VEGF at a level of at least 10 pg/mL of the liquid bioactive fraction.

In some forms, liquid bioactive fraction compositions of the present disclosure also have the following characteristics:

an endotoxin level of less than about 10 EU/ml;

less than about 25 mg/dL of hemoglobin;

about 4 to 6 g/dL total protein;

an osmolarity of about 260 to 340 mmol/kg; and/or a pH between 6.8 and 7.8.

These characteristics can be present in the raw platelet lysate composition (potentially also after solids removal by centrifugation or otherwise and sterilization), the fibrinogen-depleted liquid bioactive fraction recovered after the clotting and liquid/solid separation (and potentially sterilization), or the fibrinogen-depleted liquid bioactive fraction after depth and/or other filtration to remove suspended solids (and potentially sterilization), as described above. Also, because preferred forms of processing do not need to employ detergent as a processing agent, these compositions can be free or essentially free from detergent residues.

In some modes of operation, the procedures utilized to make the fibrinogen-depleted, filtered (e.g. depth-filtered), liquid bioactive fraction composition of the present disclosure result in reductions in the levels of growth factors, interleukins, interferons and/or tumor necrosis factors identified herein. As examples, in certain embodiments, depth or other filtration of the fibrinogen-depleted fraction is conducted to remove suspended solids, and results in:

at least a 20% reduction in the level (e.g. in pg/mL) of one, some or all of TGF-beta-1, EGF, FGF-b, PDGF-AA, PDGF-BB, SDF-1α, and VEGF; and/or at least a 50% reduction in the level (e.g. in pg/mL) of TGF-beta-1; and/or at least a 30% reduction in the level (e.g. in pg/mL) of EGF; and/or at least a 20% reduction in the level (e.g. in pg/mL) of FGF-b; and/or at least a 50% reduction in the level (e.g. in pg/mL) of PDGF-AA; and/or at least a 50% reduction in the level (e.g. in pg/mL) of PDGF-BB; and/or at least a 20% reduction in the level (e.g. in pg/mL) of SDF-1α; and/or at least a 30% reduction in the level (e.g. in pg/mL) of VEGF.

In addition or alternatively, depth or other filtration can result in highly significant levels of removal of interleukin-17 (IL-17). In certain embodiments, the level of IL-17 after depth or other filtration to remove particulate, and also potentially in the final, sterilized liquid bioactive fraction product, is less than about 1 picogram/ml, more preferably less than about 0.75 picograms/ml, and even more preferably less than about 0.5 picograms/ml. IL-17 is an inflammatory cytokine that also cascades in triggering the release of other inflammatory cytokines. Preferred products having low levels of IL-17 as identified herein can be put to use with little or no inflammatory activity stemming from the presence of IL-17.

In addition or alternatively, the depth or other filtration of the fibrinogen-depleted fraction to remove suspended solids can result in a liquid bioactive fraction product that has a concentration of PDGF-BB of less than 1000 pg/mL, a concentration of PDGF-AA of less than 3000 pg/mL, a concentration of TGF-β1 of at least 5000 pg/mL, and/or a concentration of VEGF of less than 300 pg/mL. These values can also be present in a sterilized product prepared (e.g. by sterile filtration) after the depth or other filtration to remove suspended solids.

In accordance with some modes disclosed herein the liquid bioactive fraction described herein can be processed so as to beneficially retain plasma components. Plasma components that may be retained by the liquid bioactive fraction include: globulins, albumin, triglycerides, glucose, sodium, and/or calcium. In some forms, the liquid bioactive fraction contains one or more such plasma components, and potentially all of them, while also having the following characteristics:

FGF-2 at a level of at least 200 pg/mL of the liquid bioactive fraction;

EGF at a level of at least 1800 pg/mL of the liquid bioactive fraction;

PDGF-AA at a level of at least 24,000 pg/mL of the liquid bioactive fraction;

PDGF-BB at a level of at least 50 ng/mL of the liquid bioactive fraction;

VEGF at a level of at least 500 pg/mL of the liquid bioactive fraction;

TGF-β1 at a level of at least 60 ng/mL of the liquid bioactive fraction; and

Fibrinogen at a level of less than 2.5 μg/mL of the liquid bioactive fraction.

Figure 2:
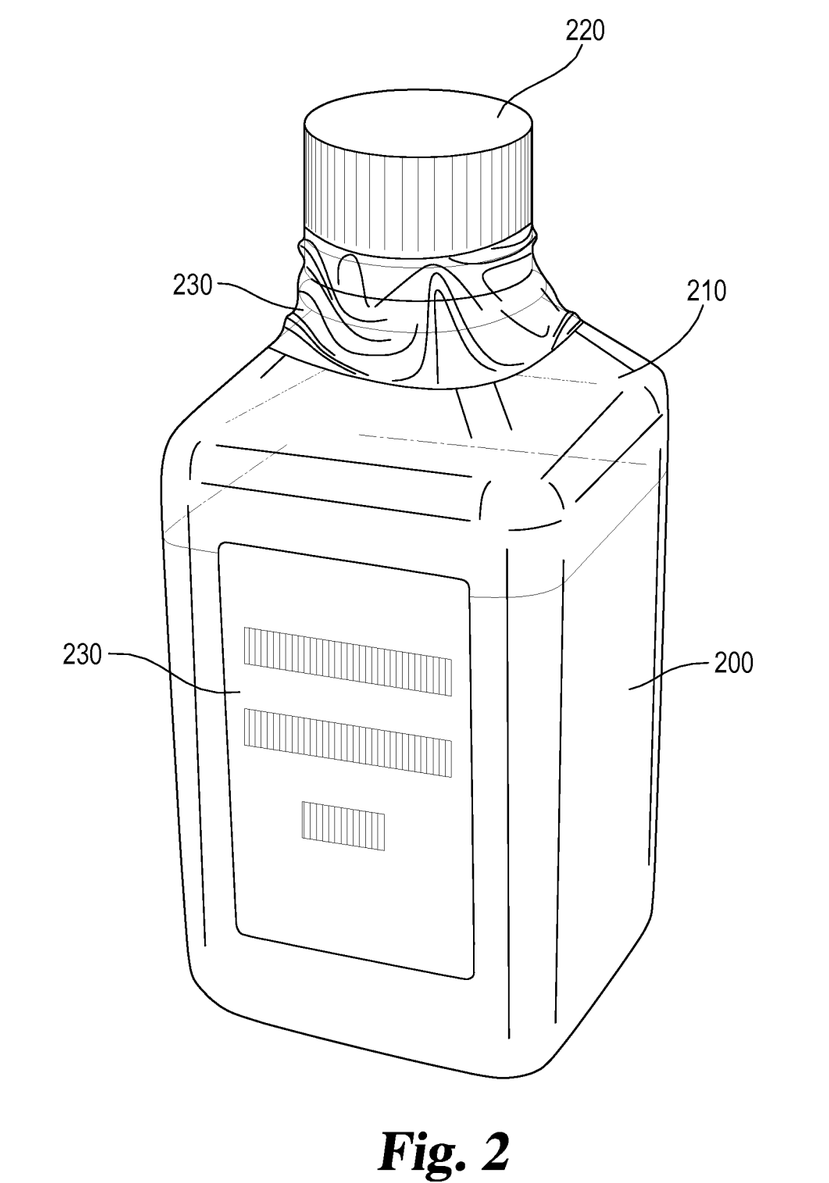
FIG. 2 is a perspective view of one embodiment of a liquid bioactive fraction of the present disclosure in a sterile package.

In some forms, liquid bioactive fraction compositions of the present disclosure may be packaged in a sterile package for storage or delivery. The liquid bioactive fraction can be packaged at its full recovered concentration, or it may be diluted with water or an aqueous medium for packaging and later use, for example dilutions to 90% to 10% of the original concentration of the liquid bioactive fraction can be prepared, and such diluted compositions, and their resulting corresponding reductions in the component levels specified herein, form additional embodiments disclosed herein. One embodiment of such packaging is illustrated in FIG. 2. In accordance with some forms of practicing the disclosure, the composition 200 is stored in a sterile media bottle 210. Sterile media bottles may, for example, have a volume capacity in the range of 50 mL to 5000 mL. As examples, 60 mL, 125 mL, 250 mL, 500 mL, 1000 mL, or 2000 mL bottles may be used. In some forms, cap 220 of sterile media bottle 210 is protected by shrink wrap 230. In some forms, the bottle is shrink wrapped. In certain embodiments, the bottle is labeled with a finished product label 240. In some forms, the bottle is placed in a product box with dry ice.

In certain embodiments, the liquid bioactive fraction composition of the present disclosure may be combined with other ingredients to form a cell culture medium. Such a cell culture medium comprises the liquid bioactive fraction of the present disclosure mixed with other nutrients or media for cell culture, including for example those as found in known cell culture media such as Minimum Essential Medium (MEM), or Dulbecco's Modified Eagle Medium (DMEM). A cell culture medium according to the present disclosure is formulated to provide nutrients (e.g. growth factors, etc.) necessary for the growth or maintenance of cells including for example stem and/or progenitor cells, such as mesenchymal stem cells. Such a cell culture medium, in preferred forms, is free from added heparin and is nonetheless free from any clotted material (e.g. as would be evidenced by the appearance of clot particles visible to the naked eye—without magnification).

In other embodiments, the liquid bioactive fraction composition of the present disclosure, or a fraction thereof, can be used as a therapeutic substance. For example, the composition can be used as a therapeutic substance for medical treatments, including for treatment of diseased or damaged tissue such as nerve, tendon, bone, muscle, skin (e.g. wound healing), connective, ocular and/or cardiovascular (e.g. heart or aorta) tissue. The liquid bioactive fraction described herein or compositions including it can be delivered to these or other tissues by any suitable means including for example injection or other surgical implantation. In certain uses, in treating ocular tissue, the liquid bioactive composition or a composition including it is applied to the surface of an eye (e.g. in the form of liquid drops), for example in the treatment of ocular surface defects or diseases, such as ocular graft versus host disease (ocular GVHD), corneal ulcers, dry eye (Keratoconjunctivitis Sicca), or corneal repair after surgery or injury.

In other embodiments, the liquid bioactive fraction composition of the present disclosure, or a fraction thereof, can be used as a therapeutic substance. For example, the composition can be used as a therapeutic substance for medical treatments, including for treatment of diseased or damaged tissue such as nerve, tendon, bone, muscle, skin (e.g. wound healing), connective, ocular and/or cardiovascular (e.g. heart or aorta) tissue. The liquid bioactive fraction described herein or compositions including it can be delivered to these or other tissues by any suitable means including for example injection or other surgical implantation. In certain uses, in treating ocular tissue, the liquid bioactive composition or a composition including it is applied to the surface of an eye (e.g. in the form of liquid drops), for example in the treatment of ocular surface defects or diseases, such as ocular graft versus host disease (ocular GVHD), corneal ulcers, dry eye (Keratoconjunctivitis Sicca), or corneal repair after surgery or injury.

In accordance with certain inventive variants, the liquid bioactive fraction of the present disclosure is used to treat a mammalian patient (e.g. human, canine, feline, equine, etc.). In certain embodiments the liquid bioactive fraction is allogeneic with respect to the target patient, in other embodiments the liquid bioactive fraction is xenogenic to with respect to the target patient. For example, in certain embodiments, a platelet lysate composition derived from human platelets may be used to treat a canine patient. It is also envisioned that a platelet lysate composition derived from canine platelets may be used to treat a canine patient, and that a platelet lysate composition derived from human platelets may be used to treat a human patient. In some forms, the patient is suffering from Keratoconjunctivitis Sicca. In accordance with certain inventive variants, the liquid bioactive fraction of the present disclosure is used to treat a canine patient suffering from Keratoconjunctivitis Sicca. The canine patient may be any breed of canine, breeds commonly affected by Keratoconjunctivitis Sicca include: cavalier king charles spaniel, bulldog, Chinese shar-pei, lhasa apso, shih tzu, west highland white terrier, pug, bloodhound, cocker spaniel, Pekingese, boston terrier, miniature schnauzer, and samoyed.

Figure 3:
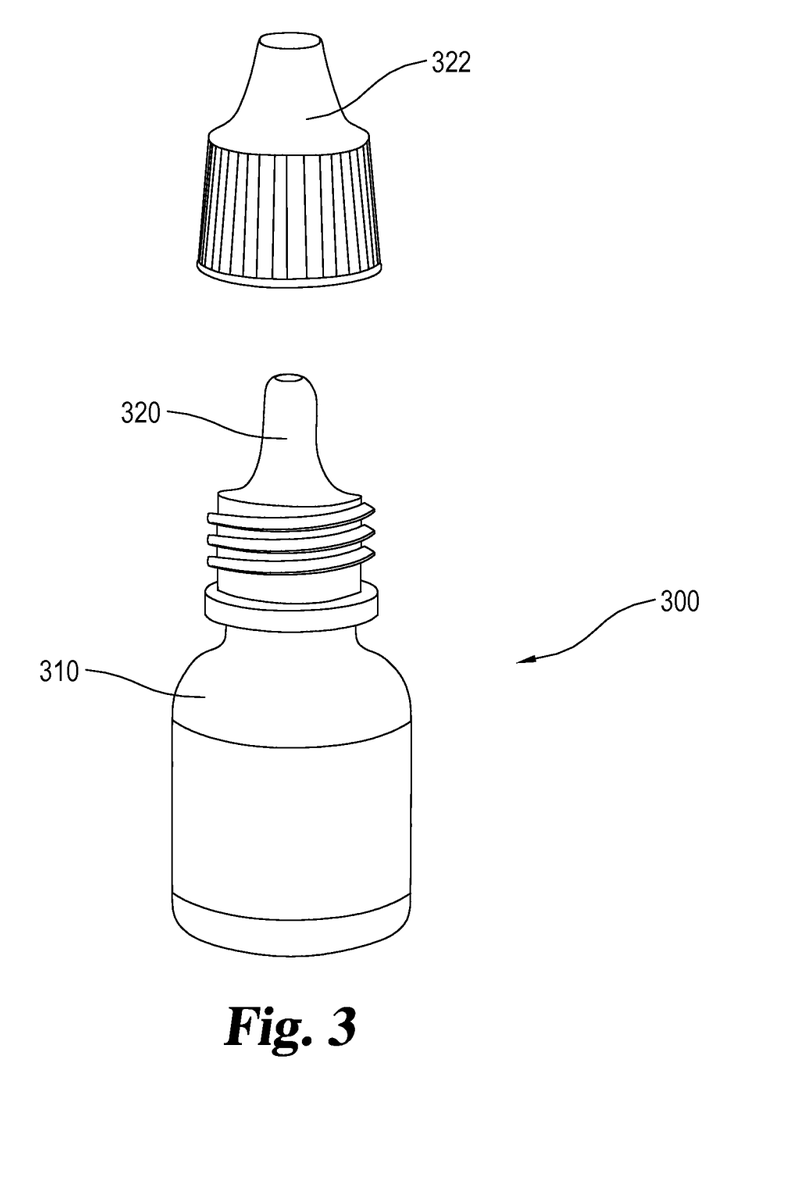
FIG. 3 is a perspective view of one embodiment of a liquid bioactive fraction of the present disclosure in a dropper bottle.

In certain embodiments the human platelet lysate containing liquid bioactive fraction is stored in a liquid delivery device configured to deliver the liquid bioactive fraction to a patient's eye. In some forms, the liquid delivery device is a sterile container. FIG. 3 illustrates one embodiment of a liquid delivery device. In the illustrated embodiment the liquid bioactive fraction is stored within device 300. Device 300 has a storage portion 310 and a dispersal portion 320. In the illustrated embodiment, dispersal portion 320 may optionally be covered with lid 322. Dispersal portion 320 may be configured so as to dispense a portion of liquid bioactive fraction (e.g. individual drops). In some forms, storage portion 310 comprises a deformable plastic material which can be squeezed by a user. Other suitable liquid delivery devices include but are not limited to: eye droppers, and pipettes.

In accordance with certain embodiments the liquid bioactive fraction of the present invention is formulated into an ointment. In some forms, a hPL containing ointment is applied topically to an affected area (e.g. a patients eye).

The liquid bioactive composition can also be used for other purposes, including for example as a cryopreservative for cells. In such cryopreservative uses, the liquid bioactive composition can be incorporated in a cellular suspension composition, the cellular suspension composition can be cryopreserved to preserve the viability of the cells. The cells can be any of a variety of cells, including stem cells such as mesenchymal stem cells, progenitor cells, or others. The cryopreservation can be conducted in a suitable vessel, such as a bag or vial.

In addition to deriving products from the recovered liquid bioactive fraction derived from the lysed platelet concentrate, valuable products can also be made from the solid clot material formed during the clotting and liquid-solid separation. In certain modes, the separated solid clot material has been discovered to also be rich in growth factors, and to contain sufficient amounts of fibrinogen and clotting factors to serve as a clottable vehicle, for example in biological adhesives, and/or to serve as a hemostatic material for medical applications. For these or other purposes, the recovered solid clot material can be stored in a refrigerated or frozen condition and/or can be lyophilized to form a dry material that can optionally be reduced to a powder form. For medical, diagnostic, research, or other applications, the solid clot material or fractions derived therefrom can be sterilized by any suitable means including for example by exposure to radiation or chemical sterilants (e.g. ethylene oxide).

As well, in addition to the recovery of the liquid bioactive fraction, and potentially also products made from the solid clot material formed during the clotting and liquid-solid separation discussed above, bio active substances such as growth factors or other proteins can be recovered individually or in mixtures from the filter or filters used to process the platelet lysate. This can recover additional value from the original starting material. Illustratively, a depth filter used in filtering the platelet lysate composition (e.g. a depth filter as described hereinabove), can thereafter be processed to recover one or more growth factors or other bioactive substances caught on the filter. This can be accomplished in any suitable manner. Illustratively, one or more proteins, such as growth factors, can be eluted from the filter by passage of an eluting liquid through the filter so as to overcome the attraction of the protein(s) to the filter media and thereby generate an eluate stream containing the protein(s). Where a charged (e.g. positively charged) depth filter is used, which retains proteins based at least in part on a charge interaction between the protein(s) and the charged filter media, the protein(s) may be recovered from the filter media by elution with salt solution(s), a change in the pH of the elution liquid (relative to that used during the initial filtration), or with an affinity elution medium (containing a ligand(s) for the protein(s) to be eluted). Gradient elution (e.g. with salt or pH gradients) may be used to sequentially elute fractions that are purified for or enriched in a specific protein or proteins of interest. The recovered protein or protein(s) may for example be any of those identified herein, preferably one or more of the growth factors, interleukins, interferons, and/or tumor necrosis factors identified herein. These may be used for example for therapeutic, diagnostic or research purposes. After recovery from the filtration media, they may optionally be purified and/or sterilized for these or other purposes.

For the purpose of promoting further understanding of aspects of the present disclosure and their features and advantages, the following specific examples are provided. It will be understood that these examples are illustrative, and not limiting, of embodiments of the present disclosure.

EXAMPLES

Example 1

Preparation of Human Platelet Lysate Composition

Disease-screened apheresed human platelet units (obtained from peripheral blood) that have just expired after a 5-day shelf life are collected and frozen at −20° C. in a freezer until use. A number of the units (e.g. about 10 units) are removed from the freezer and thawed at room temperature, thus lysing the platelets and forming a "raw hPL" composition. The raw hPL from the selected units is pooled into a bag. Calcium chloride is added to the pooled raw hPL at a level of 0.7 grams/L (approximately 6 mM $CaCl_2$) and then thoroughly mixed with the raw hPL on a shaker at room temperature for 2 hours. After mixing, the $CaCl_2$-treated raw hPL is allowed to clot overnight at room temperature, during which a firm, substantially homogeneous clotted gel mass forms from the volume of raw hPL.

While remaining closed, the bag containing the gel clot of raw hPL is manually pressed by hand to express liquid from the gel clot. This pressing is thoroughly done, resulting in a solid clot mass at one end of the bag and a separate liquid volume at the other end of the bag, adjacent an outlet spout. The separated liquid represents approximately 75-80% of the volume of the original, pooled raw hPL, and the solid clot material represents the remainder. The liquid is transferred from the bag to a second, refrigerated bag having a volume of 100 L. A sufficient number of such thaw-pool-clot-express runs are conducted to fill the refrigerated 100 L bag with liquid.

The liquid in the 100 L bag is connected aseptically to and processed through a filter train constituted of a first depth filter having a filter medium with a positive surface charge and a nominal micron rating of between 3 and 0.2 microns and a second depth filter having a filter medium with a positive surface charge and a nominal micron rating of between 0.1 and 0.001 microns. The filtration is conducted with a filtrate flux rate of about 100 liters per square meter of filter surface area per hour ("LMH"). The first depth filter is provided by a Millistack Pod Filter, Grade C0 Series HC Depth Filter, and the second depth filter is provided by a Millistack Pod Filter, Grade XO Series HC Depth Filter, both commercially available from Millipore Corporation. Each of these filters has a membrane composed of mixed esters of cellulose and filter media composed of cellulose fibers with an inorganic filter aid (diatomaceous earth). Prior to processing the 100 L bag material, the filter train is primed with sterile, distilled water. The hPL liquid exiting the filter train is collected into a second 100 L bag.

The second 100 L hPL bag is aseptically connected to and pumped through a sterile filter into smaller containers, for example 100 mL or 500 mL jars (e.g. Nalgene jars). This can be done under sterile fill conditions. The jars can be shrink-wrapped to cover their capped ends, and labeled.

An hPL product produced in accordance with this Example has a compositional profile as specified herein and can be used as a supplement to cell culture media without the requirement of adding heparin to prevent clot formation. The addition of this hPL product to a cell culture medium results in an essentially clot-free medium, even without the addition of heparin. The cell culture media so produced exhibit excellent properties in the culture of cells, including but not limited to bone marrow mesenchymal cells, adipocyte stem cells, placenta derived mesenchymal stem cells, and muscle-derived stem or progenitor cells, with relatively high cell counts or percent confluence after a given culture period being obtainable in preferred uses.

Example 2

Preparation of Human Platelet Lysate Composition

Disease-screened apheresed human platelet units (obtained from peripheral blood) that have just expired after a 5-day shelf life are collected and frozen at −20° C. in a freezer until use. A number of the units (e.g. about 23 units) are removed from the freezer and thawed at room temperature, thus lysing the platelets and forming a "raw hPL" composition. The raw hPL from the selected units is pooled into a bag. Calcium chloride is added to the pooled raw hPL at a level of 0.75 grams/L (approximately 6 mM $CaCl_2$) and then thoroughly mixed with the raw hPL on a shaker at room temperature for 2 hours. After mixing, the $CaCl_2$-treated raw hPL is allowed to clot overnight at room temperature, during which a firm, substantially homogeneous clotted gel mass forms from the volume of raw hPL.

While remaining closed, the bag containing the gel clot of raw hPL is pressed to express liquid from the gel clot. This pressing is thoroughly done, resulting in a solid clot mass at one end of the bag and a separate liquid volume at the other end of the bag, adjacent an outlet spout. The separated liquid represents approximately 75-80% of the volume of the original, pooled raw hPL, and the solid clot material represents the remainder. The liquid is transferred from the bag to a second, fill bag having a volume of 25 L. A sufficient number of such thaw-pool-clot-express runs are conducted to fill the 25 L fill bag with liquid.

The 25 L fill bag is stored overnight in a 4° C. laboratory refrigerator. A peristaltic pump is used to transfer the fluid from the 25 L fill bag, through a pre-filter (25 µm) and a sterile filter (0.2 µm). The filtered liquid is pooled into a collection bag. The filtered liquid (hPl) is then aliquoted into sterile containers (e.g 100 mL or 500 mL Nalgene jars). This can be done under sterile fill conditions. The jars can be shrink-wrapped to cover their capped ends, and labeled.

An hPL product produced in accordance with this Example has a compositional profile as specified herein and can be used as a supplement to cell culture media without the requirement of adding heparin to prevent clot formation, and can also be put to use in the other applications identified herein for liquid bioactive fractions. The addition of this hPL product to a cell culture medium results in an essentially clot-free medium, even without the addition of heparin. The cell culture media so produced exhibit excellent properties in the culture of cells, including but not limited to bone marrow mesenchymal cells, adipocyte stem cells, placenta derived mesenchymal stem cells, and muscle-derived stem or progenitor cells, with relatively high cell counts or percent confluence after a given culture period being obtainable in preferred uses.

Example 3

Preparation of Canine Platelet Lysate Composition

A canine platelet lysate (CPL) composition can be prepared substantially as described above. Generally, preparation of CPL composition begins with preparation of disease-screened apheresed canine platelet units obtained from peripheral blood. As detailed above, such platelet unit may be freshly prepared or may be obtained from an expired platelet unit. The platelet unit is frozen at −20° C. in a freezer until use. A number of the units (e.g. about 10 units) are removed from the freezer and thawed at room temperature, thus lysing the platelets and forming a "raw CPL" composition. The raw CPL from the selected units is pooled into a bag. Calcium chloride is added to the pooled raw CPL at a level of 0.7 grams/L (approximately 6 mM CaCl2) and then thoroughly mixed with the raw CPL on a shaker at room temperature for 2 hours. After mixing, the CaCl2-treated raw CPL is allowed to clot overnight at room temperature, during which a firm, substantially homogeneous clotted gel mass forms from the volume of raw CPL.

While remaining closed, the bag containing the gel clot of raw CPL is manually pressed by hand to express liquid from the gel clot. This pressing is thoroughly done, resulting in a solid clot mass at one end of the bag and a separate liquid volume at the other end of the bag, adjacent an outlet spout. The separated liquid represents approximately 75-80% of the volume of the original, pooled raw CPL, and the solid clot material represents the remainder. The liquid is transferred from the bag to a second, refrigerated bag having a volume of 100 L. A sufficient number of such thaw-pool-clot-express runs are conducted to fill the refrigerated 100 L bag with liquid.

The collected liquid (e.g. liquid bioactive fraction) is then passed through a sterile filter. In some forms, the collected liquid is passed through a series of depth filters as described in Example 1. The filtered liquid (cPL) is then aliquoted into sterile containers (e.g. 100 mL or 500 mL Nalgene jars). This can be done under sterile fill conditions. The jars can be shrink-wrapped to cover their capped ends, and labeled.

A CPL product produced in accordance with this Example has a compositional profile as specified herein and can be used as a supplement to cell culture media without the requirement of adding heparin to prevent clot formation, and can also be put to use in the other applications identified herein for liquid bioactive fractions. The addition of this CPL product to a cell culture medium results in an essentially clot-free medium, even without the addition of heparin. The cell culture media so produced exhibit excellent properties in the culture of cells, including but not limited to bone marrow mesenchymal cells, adipocyte stem cells, placenta derived mesenchymal stem cells, and muscle-derived stem or progenitor cells, with relatively high cell counts or percent confluence after a given culture period being obtainable in preferred uses. The CPL solution may also be used as a therapeutic as described herein.

The use of the terms "a" and "an" and "the" and similar referents in the context of describing the invention especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

All publications and patent applications cited in this specification are herein incorporated by reference as if each individual publication or patent application were specifically and individually indicated to be incorporated by reference. Further, any theory, mechanism of operation, proof, or finding stated herein is meant to further enhance understanding of the present invention, and is not intended to limit the present invention in any way to such theory, mechanism of operation, proof, or finding. While the invention has been illustrated and described in detail in the drawings and foregoing description, the same is to be considered as illustrative and not restrictive in character, it being understood that only selected embodiments have been shown and described and that all equivalents, changes, and modifications that come within the spirit of the inventions as defined herein or by the following claims are desired to be protected.

The invention claimed is:

1. A composition comprising:
    A bioactive fraction of a human blood-derived platelet concentrate, the platelet concentrate containing human platelets and human plasma, the bioactive fraction comprising native components released by lysis or activation of the human platelets and native components of the human plasma, the bioactive fraction including fibrinogen at a level of less than 20,000 ng/mL, albumin, globulin and at least one of TGF-β1, EGF, FGF-basic, PDGF-AA, PDGF-BB, SDF-1α, and VEGF.

2. The composition of claim 1, wherein the fibrinogen is present at a level of less than 10,000 ng/mL.

3. The composition of claim 1, which comprises each of said TGF-β1, EGF, FGF-basic, PDGF-AA, PDGF-BB, SDF-1α, and VEGF.

4. The composition of claim 1, wherein the composition is free from added heparin.

5. The composition of claim 1, wherein the bioactive fraction also includes at least one of IL-1b, IL-6, IL-8, IL-10, IL-13, IL-17, IFN-gamma, and TNF-alpha native to the platelet concentrate.

6. The composition of claim 1, wherein the bioactive fraction is a liquid bioactive fraction, and wherein the composition includes:
    about 0.5 to 2.5 g/dL globulins;
    about 2 to 5 g/dL albumin;
    about 100 to 200 mmol/L sodium;
    about 50 to 120 mg/dL triglycerides; and/or
    about 150 to 300 mg/dL glucose.

7. The composition of claim 1, which is free from detergent residues.

8. The composition of claim 1, wherein the bioactive fraction is a liquid bioactive fraction, and wherein the concentration of PDGF-BB is less than 1000 pg/mL.

9. The composition of claim 1, wherein the bioactive fraction is a liquid bioactive fraction, and wherein the concentration of PDGF-AA is less than 3000 pg/mL.

10. The composition of claim 1, wherein the bioactive fraction is a liquid bioactive fraction, and wherein the concentration of TGF-β1 is at least 5000 pg/mL.

11. The composition of claim 1, wherein the bioactive fraction is a liquid bioactive fraction, and wherein the concentration of VEGF is less than 300 pg/mL.

12. The composition of claim 1, wherein the bioactive fraction is a liquid bioactive fraction, and wherein the native components include:
    albumin at a level of at least 2 mg/dL of the liquid bioactive fraction;
    globulin at a level of at least 1 g/dL of the liquid bioactive fraction;
    TGF-β1 at a level of at least 5000 pg/mL of the liquid bioactive fraction;
    EGF at a level of at least 20 pg/mL of the liquid bioactive fraction;
    FGF-beta at a level of at least 5 pg/mL of the liquid bioactive fraction;
    PDGF-AA at a level of at least 200 pg/mL of the liquid bioactive fraction;
    PDGF-BB at a level of at least 50 pg/mL of the liquid bioactive fraction;
    SDF-1α at a level of at least 100 pg/mL of the liquid bioactive fraction; and
    VEGF at a level of at least 10 pg/mL of the liquid bioactive fraction.

13. The composition of claim 1, wherein:
    the composition has an osmolarity between 260-340 mmol/kg.

14. The composition of claim 1, wherein:
    the composition has a pH in the range of 6.8 to 7.8.

15. The composition of claim 1, wherein:
    the composition is free of heparin not native to the platelet concentrate.

16. A cell culture medium comprising a composition according to claim 1.

17. The cell culture medium of claim 16, which is free from added heparin.

18. The composition of claim 1, wherein said composition is stored within a liquid delivery device.

19. The composition of claim 18, wherein said liquid delivery device comprises an eye dropper.

20. The composition of claim 1 wherein said composition is effective to treat a disease or diseased state in a canine patient.

21. The composition of claim 20 wherein, said diseased state comprises keratoconjunctivitis sicca.

22. The composition of claim 1, wherein the bioactive fraction is a liquid bioactive fraction, and wherein the composition comprises:
   FGF-2 at a level between about 200 pg/mL to about 350 pg/mL;
   EGF at a level of between about 1800 pg/mL to about 3100 pg/mL;
   PDGF-AA at a level of between about 24,000 pg/mL to about 28,000 pg/mL;
   PDGF-BB at a level of between about 50 ng/mL to about 80 ng/mL;
   VEGF at a level of between about 500 pg/mL to about 800 pg/mL;
   TGF-b at a level of between about 60 ng/mL to about 90 ng/mL; and
   Fibrinogen at a level of less than 2.5 µg/mL.

23. The composition of claim 5, wherein the bioactive fraction also includes each of, IL-1b, IL-6, IL-8, IL-10, IL-13, IL-17, IFN-gamma, and TNF-alpha native to the platelet concentrate.

24. The composition of claim 6, wherein the bioactive fraction is a liquid bioactive fraction, and wherein the composition includes:
   about 1 to 2 g/dL globulins;
   about 3 to 4 g/dL albumin;
   about 120 to about 160 mmol/L sodium;
   about 60 to 110 mg/dL triglycerides; and/or
   about 150 to 250 mg/dL glucose.

\* \* \* \* \*